US006187319B1

(12) United States Patent
Herrmann et al.

(10) Patent No.: US 6,187,319 B1
(45) Date of Patent: Feb. 13, 2001

(54) CROSS-PROTECTIVE ROTAVIRUS VACCINE

(75) Inventors: John E. Herrmann; Shan Lu, both of Northborough, MA (US)

(73) Assignee: University of Massachusetts, Boston, MA (US)

( * ) Notice: Under 35 U.S.C. 154(b), the term of this patent shall be extended for 0 days.

(21) Appl. No.: 09/088,216

(22) Filed: Jun. 1, 1998

(51) Int. Cl.[7] .................................................. A61K 39/15
(52) U.S. Cl. .......................................... 424/215.1; 514/44
(58) Field of Search ............................. 424/204.1, 215.1; 514/44

(56) References Cited

U.S. PATENT DOCUMENTS 5,620,896 4/1997 Hermann et al. ................. 435/320.1

OTHER PUBLICATIONS

Andrew et al., "The Roles of Influenza Virus Haemagglutinin an Nucleoprotein in Protection: Analysis Using Vaccinia Virus Recombinants", Scand. J. Immunol. 25:21–28, 1987.

Conner et al., "Rotavirus Vaccines and Vaccination Potential", Current Topics in Microbiology and Immunology 185:297–305, 1994.

Dharakul et al., "Immunization with Baculovirus–Expressed Recombinant Rotavirus Proteins VP1, VP6, and VP7 Induces CD8+ T Lymphocytes . . . ", J. of Virology 5928–5932, 1991.

Herrmann et al., "DNA Vaccines Against Rotavirus Infections", Arch Virol Suppl. 12:207–215, 1996.

Herrmann et al., "Protection Against Rotavirus Infections by DNA Vaccination", JID Suppl 1 174:S93–S97, 1996.

Banos, et al., Journal of Virology, 71(1):419–426, Jan. 1997.*

Chen et al., Vaccine, 15(8):899–902, Jun. 1997.*

Murphy, F., "Virus Taxonomy", pp. 15–57 in Fields Virology, ed. Fields et al., Kippincott–Raven, Philadelphia, 1996.*

Kapikian et al., The Journal of Infectious Dieseases, 153(5):815–822, May 1986.*

Moore et al., Vaccine, 13(8):1741–1749, 1995.*

Yan et al., Vaccine, 13(7):645–651, May 1995.*

* cited by examiner

*Primary Examiner*—Anthony C. Caputa
*Assistant Examiner*—Brenda G. Brumback
(74) *Attorney, Agent, or Firm*—Fish & Richardson P.C.

(57) ABSTRACT

A method of producing an effective immune response in an animal against a first rotavirus, by (1) identifying an animal susceptible to or having a first rotavirus infection; and (2) administering to the animal an isolated VP6 polypeptide of a second rotavirus sufficient to produce an effective immune response against the first rotavirus, the second rotavirus capable of infecting a different species than the first rotavirus.

27 Claims, 1 Drawing Sheet

CROSS-PROTECTIVE ROTAVIRUS VACCINE

STATEMENT AS TO FEDERALLY SPONSORED RESEARCH

This invention was made with Government support under National Institutes of Health grant RO1AI39637.

BACKGROUND OF THE INVENTION

The invention relates to rotavirus vaccines.

Rotavirus infections are ubiquitous throughout mammalian and avian species. The viruses typically appear to be species-specific in the wild. Infection occurs after ingestion of viral particles and is restricted to the mature absorptive epithelial cells on the villi of the small intestine. Multiplication of rotaviruses within these cells results in lysis, and eventual loss of normal villous structure. Copious acute watery diarrhea occurs as a result of intestinal damage and replacement of absorptive cells by secreting cells from the villous crypts in the intestine.

Rotaviruses have a multi-shelled capsid and a segmented RNA genome. Among the rotavirus structural proteins are VP7, the most abundant outer capsid protein in the virus particle, and VP6, the major component of the inner capsid.

SUMMARY OF THE INVENTION

The invention is based on the discovery that an isolated VP6 polypeptide from a rotavirus which naturally infects one species (such as a cow) can produce an effective immune response against a rotavirus which naturally infects another species (such as a mouse or human), so that VP6 is an effective cross-protective rotavirus vaccine. An isolated VP6 polypeptide is a VP6 polypeptide that is in an environment other than its natural environment, e.g., by purification or simply as a result of enhancing the percentage of VP6 present ("spiking") in naturally occurring mixtures such as viral or infected cell preparations.

In general, the invention features a method of producing an effective immune response in an animal (for example, cows, pigs, horses, and especially humans) against a first rotavirus by (1) identifying an animal susceptible to or having a first rotavirus infection; and (2) administering (e.g., orally) to the animal an isolated VP6 polypeptide of a second rotavirus sufficient to produce an effective immune response against the first rotavirus, the second rotavirus capable of infecting a different species than the first rotavirus. For example, a cow, pig, or horse rotavirus VP6 is administered to a human in order to elicit an effective immune response against a human rotavirus. Alternatively, a human, cow, or pig rotavirus VP6 is administered to a horse in order to elicit an effective immune response against a horse rotavirus. In addition, the VP6 polypeptide can cross-react with antibodies produced from the animal (e.g., a human) when infected with the first rotavirus (e.g., a human rotavirus).

In some embodiments of the above method, the animal is of a first species, and the second rotavirus is capable of infecting a second species different from the first species and incapable of infecting the first species.

An immune response against the first rotavirus is considered effective if viral loads or the symptoms of infection are reduced in the animal when the VP6 is administered to the animal as compared to when the VP6 is not administered. Preferably, such reductions are statistically significant, as shown in the Example section below. For example, an immune response that protects against viral infection is "effective."

The isolated VP6 polypeptide of the second rotavirus can be administered to the animal via an expression vector (e.g., a DNA plasmid) comprising a sequence encoding the VP6 polypeptide of the second rotavirus. When the isolated VP6 is administered as a DNA plasmid, DNA delivery can be facilitated by encapsulating the DNA in a microparticle, e.g., one made of poly(lactide-co-glycolide) (PLG).

An expression vector encoding the isolated VP6 polypeptide is not limited to a DNA plasmid. For example, an expression vector can be a virus, such as a retrovirus. Whether in the form of a plasmid or virus, the expression vector can further contain a cytomegalovirus intron A transcriptional regulatory sequence and a cytomegalovirus enhacer and promoter sequence operably linked to the sequence encoding the VP6 polypeptide of the second rotavirus.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
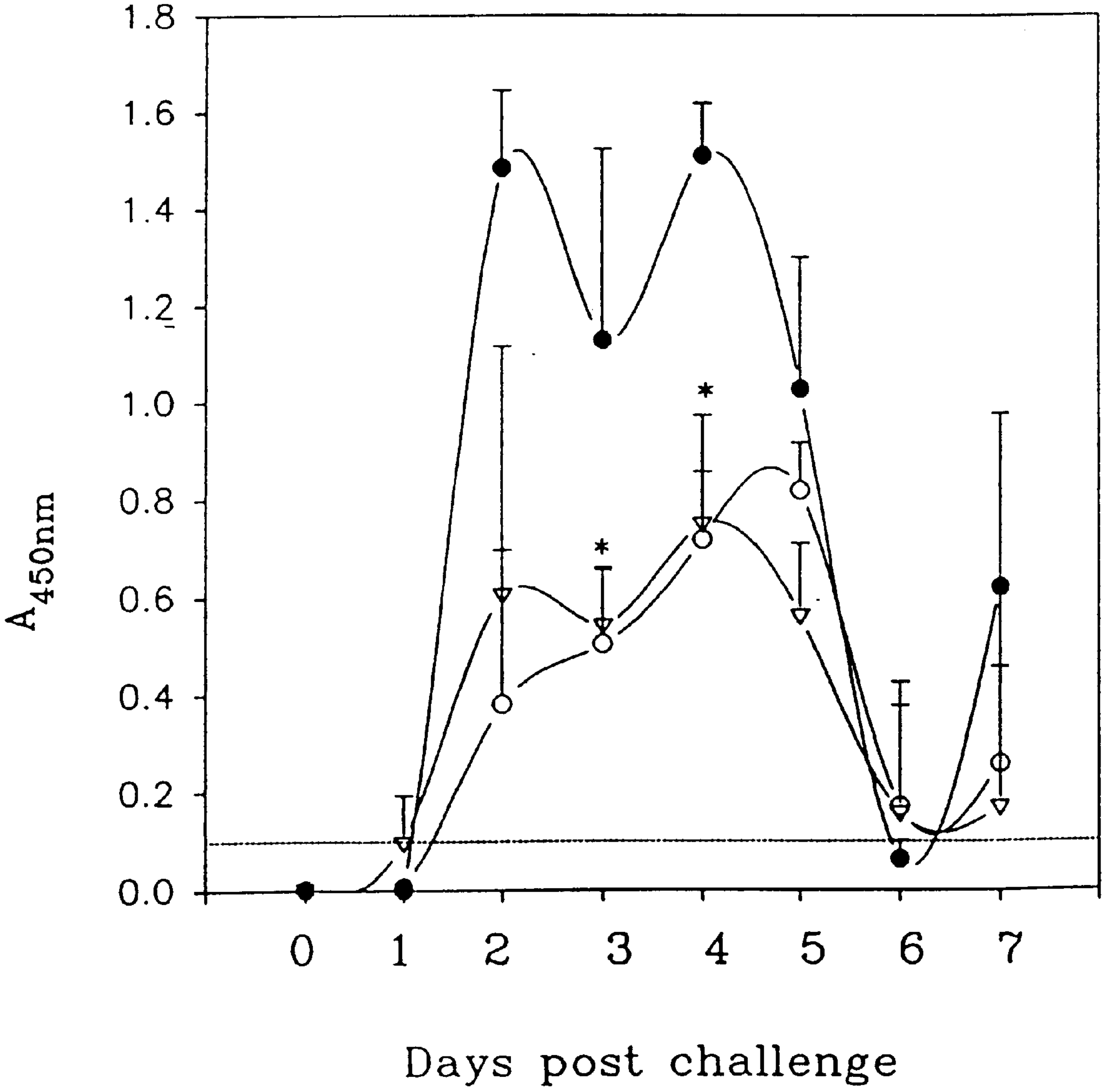
FIG. 1 is a graph of days post-challenge versus challenge virus titer in mice immunized with PLG-encapsulated DNA vaccines.

The invention relates to the use of an isolated rotavirus VP6 polypeptide as a cross-protective rotavirus vaccine.

I. Production and Isolation of VP6 Polypeptides

A. Production

VP6 polypeptides can be isolated from any rotavirus that can be propagated and purified. Once the rotavirus is purified, the virus particles can be disrupted, and the VP6 isolated by one or more standard procedures, such as high performance liquid chromatography or differential salt precipitation.

Alternatively, the VP6 can be produced recombinantly. The VP6 open reading frame from a variety of rotavirus isolates are known. See, for example, the cloned VP6 polypeptides disclosed in U.S. Pat. No. 5,620,896. Other VP6 sequences include the following:

GenBank Accession No. X53667 (bovine)

(SEQ ID NO:1)

MDVLYSLSKTLKDARDKIVEGTLYSNVSDLIQQFNQMIITMNGNE

FQTGGIGNLPIRNWNFDFGLLGTTLLNLDANYVETARNTIDYFVD

-continued

FVDNVCMDEMVRESQRNGIAPQSDSLRKLSGIKFKRINFDNSSEY

IENWNLQNRRQRTGFTFHKPNIFPYSASFTLNRSQPAHDNLMGTM

WLNAGSEIQVAGFDYSCAINAPANTQQFEHIVQLRRVLTTATITL

LPDAERFSFPRVINSADGATTWYFNPVILRPNNVEVEFLLNGQII

NTYQARFGTIIARNFDTIRLSFQLMRPPNMTPAVAALFPNAQPFE

HQATVGLTLRIESAVCESVLADASETMLANVTSVRQEYAIPVGPV

FPPGMNWTDLITNYSPSREDNLQRVFTVASIRSMLVK

GenBank Accession No. M88768 (bovine)

(SEQ ID NO:2)

MDVLFSIAKTVSELKKRVVVGTIYTNVEDIIQQTNELIRTLNGST

FHTGGIGTQPQKDWVVQLPQLGTTLLNLDDNYVQSARGIIDYLAS

FIEAVCDDEMVREASRNGMQPQSPTLIALASSKFKTINFNNSSQS

IKNWSAQSRRENPVYEYKNPMVFEYRNSYILHRADQQFGNAMGLR

YYTTSNTCQIAAFDSTMAENAPNNTQRFIYHGRLKRPISNVLMKV

ERGAPNNNNPTILPDPTNQTTWLFNPVQVMNGTFTIEFYNNGQLV

DMVRNMGIATVRTFDSYRITIDMIRPAAMTQYVQQLFPVGGPYSH

QAAYMLTLSVLDATTESVLCDSHSVDYSIVANTRRDSAMPAGTVF

QPGFPWEQTLSNYTVAQEDNLERLLLVASVKRMVM

GenBank Accession No. K02086 (human)

(SEQ ID NO:3)

MEVLYSLSKTLKDARDKIVEGTLYSNVSDLIQQFNQMIVTMNGND

FQTGGIGNLPVRNWTFDFGLLGTTLLNLDANYVENARTIIEYFID

FIDNVCMDEMARESQRNGVAPQSEALRKLAGIKFKRINFDNSSEY

IENWNLQNRRQRTGFVFHKPNIFPYSASFTLNRSQPMHDNLMGTM

WLNAGSEIQVAGFDYSCAINAPANIQQFEHIVQLRRALTTATITL

LPDAERFSFPRVINSADGATTWFFNPVILRPNNVEVEFLLNGQII

NTYQARFGTIIARNFDAIRLLFQLMRPPNMTPAVNALFPQAQPFQ

HHATVGLTLRIESAVCESVLADANETLLANVTAVRQEYAIPVGPV

FPPGMNWTELITNYSPSREDNLQRVFTVASIRSMLIK

GenBank Accession No. X59843 (human)

(SEQ ID NO:4)

MDVLFSIAKTVSDLKKKVVVGTIYTNVEDVVQQTNELIRTLNGNI

FHTGGIGTQPQKEWNFQLPQLGTTLLNLDDNYVQSTRGIIDFLSS

FIEAVCDDEIVREASRNGMQPQSPALILLSSSKFKTINFNNSSQS

IKNWNAQSRRENPVYEYKNPMLFEYKNSYILQRANPQFGSVMGLR

YYTTSNTCQIAAFDSTLAENAPNNTQRFVYNGRLKRPISNVLMKI

EAGAPNISNPTILPDPNNQTTWLFNPVQLMNGTFTIEFYNNGQLI

-continued

DMVRNMGIVTVRTFDSYRITIDMIRPAAMTQYVQRIFPQGGPYHF

QATYMLTLSILDATTESVLCDSHSVEYSIVANVRRDSAMPAGTVF

QPGFPWEHTLSNYTVAQEDNLERLLLIASVKRMVM

GenBank Accession No. U82971 (porcine)

(SEQ ID NO:5)

MEVLYSLSKTLKDARDKIVEGTLYSNVSDLIQQFNQMIVTMNGND

FQTGGIGNSPVRNWNFDFGLLGTTLLNLDANYVENARTTIEYFVD

FIDNVCMDEMTRESQRSGIAPQSEALRKQSGIKFKRINFDNSSDY

IENWNLQNRRQRTGFVFHKPNILPYSASFTLNRSQPAHDNLMGTM

WINAGSEIQVAGFDYSCAFNAPANIQQFEHVVPLRRALTTATITL

LPDAERFSFPRVINSADGTTTWYFNPVILRPSNVEVEFLLNGQII

NTYQARFGTIIARNFDTIRLSFQLVRPPNMTPAVANLFPQAPPFI

FHATVGLTLRIESAVCESVLADASETLLANVTSVRQEYAIPVGPV

FPPGMNWTELITNYSPSREDNLQRVFTVASIRSMLIK

GenBank Accession No. U65988 (murine)

(SEQ ID NO:6)

MDVLYSISRTLKDARDKIVEGTLYSNVSDLIQQFNQMLVTMNGNE

FQTGGIGNLPLRNWNFDFGLLGTTLLNLDANYVESARTTIDYFVD

FIDNVCMDEMMRESQRNGIAPQSDALRKLSGVKFRRINFNNSSEY

IENWNLQNRRQRTGFTFHKPNIFPYSASFTLNRSQPQHDNLMGTM

WLNAGSEIQVAGFDYSCAINAPANIQQFEHIVQLRRVLTTATITL

LPDAERFSFPRVINSADGATTWYFNPVILRPNNVEVEFLLNGQVI

NTYQARFGTIVARNFDTIRLSFQLMRPPNMTPAVTALFPNAQPFE

HHATVGLTLRIDSAICESVLADASETMLANVTSVRQEYAIPVGPV

FPPGMNWTDLITNYSPSREDNLQRVFTVASIRSMLVK

GenBank Accession No. D16329 (avian)

(SEQ ID NO:7)

MDVLYSLAKTLKDARAKIVEGTLYTNVADIVQQVNQVINSINGST

FQTGGIGNLPVRNWTFDFGTLGTTLLNLDANYVENARTTIDYFID

FVDSVCVDEIVRESQRNGIAPQSDSLRQLSNAKYKRINYDNESEY

IENWNLQNRRQRTGYLLHKPNILPYNNSFTLTRSQPAHDNVCGTI

WLNNGSEIEIAGFDSECALNAPGNIQEFEHVVPMRRVLNNATVSL

LPYAPRLTQRAVIPTADGLNTWLFNPIILRPNNVQVEFLLNGQVI

TNYQARYGTLAARNFDSIRISFQLVRPPNMTPGVAALFPQAAPFP

NHATVGLTLKIESASCESVLSDANEPYLSIVTGLRQEYAIPVGPV

FPAGMNWTELLNNYSASREDNLQRIFTAASIRSMVIK

GenBank Accession No. D00323 (equine)

(SEQ ID NO:8)

MEVLYSISKTLKDARDKIVEGTLYSNVSDIIQQFNQIIVTMNGNE
FQTGGIGTLPIRNWTFDFGLLGTTLLNLDANYVETARTTIEYFID
FIDNVCMDEMTRESQRNGIAPQSDALRKLSGIKFKRINFDNSSEY
IENWNLQNRRQRTGFVFHKPNIFPYSASFTLNRSQPLHNDLMGTM
WLNAGSEIQVAGFDYSCAINAPANTQQFEHIVQLRRALTTATITI
LPDAERFSFPRVINSADGATTWFFNPVILRPNNVEVEFLLNGQII
NTYQARFGTIIARNFDTIRLSFQLMRPPNMTPAVNALFPQAQPFQ
HHATVGLTLRIDSAVCESVLADSNETMLAAVTAVRQEYAVPVGPV
FPPGMNWTELITNYSPSREDNLQRVFTVASIRSMLIK

GenBank Accession No. L11595 (lamb)

(SEQ ID NO:9)

MDVLYSLSKTLKDARDKIVEGTLYSNVSDLIQQFNQMIVTMNGNE
FQTGGIGNLPIRNWNFDFGLLGTTLLNLDANYVETARNTIDYFVD
FVDNVCMDEMVRESQRNGIAPQSESLRKLSGIKFKRINFDNSSEY
IENWNLQNRRQRTGFTFHKPNIFPYSASFTLNRSQPAHDNLMGTM
WLNAGSEIQVAGFDYSCAINAPANTQQFEHIVQLRRVLTTATITL
LPDAERFSFPRVINSADGATTWYFNPVILRPNNVEVEFLLNGQII
NTYQARFGTIIARNFDTIRLSFQLMRPPNMTPAVAALFPNAQPFE
HHATVGLTLRIESAVCESVLADASETMLANVTSVRQEYAIPVGPV
FPPGMNWTDLITNYSPSREDNLQRVFTVASIRSMLIK

GenBank Accession No. L33365 (simian)

(SEQ ID NO:10)

NDVLYSLSKTLKDARDKIVEGTLYSNVSDLIQQFNQMIITMNGNE
FQTGGIGNLPIRNWNFNFGLLGTTLLNLDANYVETARNTIDYFVD
FVDNVCMDEMVRESQRNGIAPQSDSLRKLSAIKFKRINFDNSSEY
IENWNLQNRRQRTGFTFHKPNIFPYSASFTLNRSQPAHDNLMGTM
WLNAGSEIQVAGFDYSCAINAPANIQQFEHIVPLRRVLTTATITL
LPDAERFSFPRVINSADGATTWFFNPVILRPNNVEVEFLLNGQII
NTYQARFGTIVARNFDTIRLSFQLMRPPNMTPAVAVLFPNAQPFE
HHATVGLTLRIESAVCESVLADASETLLANVTSVRQEYAIPVGPV
FPPGMNWTDLITNYSPSREDNLQRVFTVASIRSMLIKMDVLYSLS
KTLKDARDKIVEGTLYSNVSDLIQQFNQMIITMNGNEFQTGGIGN
LPIRNWNFNFGLLGTTLLNLDANYVETARNTIDYFVDFVDNVCMD
EMVRESQRNGIAPQSDSLRKLSAIKFKRINFDNSSEYIENWNLQN
RRQRTGFTFHKPNIFPYSASFTLNRSQPAHDNLMGTMWLNAGSEI
QVAGFDYSCAINAPANIQQFEHIVPLRRVLTTATITLLPDAERFS
FPRVINSADGATTWFFNPVILRPNNVEVEFLLNGQIINTYQARFG

-continued

TIVARNFDTIRLSFQLMRPPNMTPAVAVLFPNAQPFEHHATVGLT
LRIESAVCESVLADASETLLANVTSVRQEYAIPVGPVFPPGMNWT
DLITNYSPSREDNLQRVFTVASIRSMLIK

VP6 can be produced by transformation (transfection, transduction, or infection) of a host cell with a VP6-encoding DNA fragment in a suitable expression vehicle. Suitable expression vehicles include plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene; Lajolla, Calif.).

Those skilled in the field of molecular biology will understand that any of a wide variety of expression systems can be used to provide the recombinant protein. The precise host cell used is not critical to the invention.

Proteins and polypeptides can also be produced by plant cells. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology,* John Wiley & Sons, New York, 1994). The methods of transformation or transfection and the choice of expression vehicle will depend on the host system selected. Transformation and transfection methods are described, e.g., in Ausubel et al., Current Protocols in Molecular Biology, John Wiley & Sons, New York (1994); expression vehicles may be chosen from those provided, e.g., Pouwels et al., Cloning Vectors: A Laboratory Manual (1985), Supp. (1987).

The host cells harboring the expression vehicle can be cultured in conventional nutrient media adapted as need for activation or repression of a chosen gene, selection of transformants, or amplification of a chosen gene.

Specific initiation signals may be required for efficient translation of inserted nucleic acid sequences. These signals include the ATG initiation codon and adjacent sequences. In cases where an entire native VP6, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription or translation enhancer elements, (e.g., ones disclosed in Bittner et al., Methods in Enzymol, 153:516 [1987]).

Preferred polypeptides are those which are soluble under normal physiological conditions. Also within the invention are fusion proteins in which a portion (e.g., one or more epitopes) of VP6 is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of VP6 is joined in-frame to a nucleotide sequence encoding the fusion partner. For example, the expression vector PUR278 (Ruther et al., EMBO J 2:1791 [1983]), can be used to create lacZ fusion proteins. The PGEX vectors can be used to express foreign polypeptides as fusion proteins containing glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

A fusion protein can be readily purified by utilizing an antibody specific for the fusion protein being expressed. For example, a system described in Janknecht et al., Proc Natl Acad Sci USA 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers. The same procedure can be used for a bacterial culture.

Alternatively, VP6 or a portion thereof, can be fused to an immunoglobulin Fc domain. Such a fusion protein can be readily purified using an affinity column.

Polypeptides used in the methods of the invention, particularly short amino acid sequences containing a VP6 epitope, can also be produced by chemical synthesis (e.g., by the methods described in *Solid Phase Peptide Synthesis,* 2nd ed., [1984] The Pierce Chemical Co., Rockford, Ill.).

VP6 polypeptides useful in the methods of the invention include any protein or polypeptide sharing an epitope with a naturally occurring VP6. Such functionally related VP6 polypeptides can have additions or substitutions of amino acid residues within the VP6 amino acid sequence compared to the wild type VP6 sequence. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

VP6 variants with altered amino acid sequences can be created by making random mutations to VP6 DNA (which has been described in U.S. Pat. No. 5,620,896) using random mutagenesis techniques well known to those skilled in the art, and isolating the polypeptide in a way that yields highly antigenic VP6. Alternatively, site-directed mutations of the VP6 coding sequence can be engineered using techniques also well-known to those skilled in the art.

To design variant VP6 polypeptides, it is useful to distinguish between conserved positions and variable positions. To produce variants with increased antigenicity, it is preferable that conserved residues are not altered. Moreover, alteration of non-conserved residues are preferably conservative alterations, e.g., a basic amino acid is replaced by a different basic amino acid.

Other mutations to the VP6 coding sequence can be made to generate VP6 polypeptides that are better suited for expression, e.g., for scaled up production, in a selected host cell.

B. Isolation

Both naturally occurring and recombinant forms of VP6 can be produced as described above. Secreted forms can be isolated from the culture media, while non-secreted forms must be isolated from the host cells. Polypeptides can be isolated by affinity chromatography. In one example, an anti-VP6 antibody is attached to a column and used to isolate the VP6 polypeptide. Lysis and fractionation of VP6-harboring cells prior to affinity chromatography can be performed by standard methods (see, e.g., Ausubel et al., supra). Alternatively, a VP6 fusion protein can be constructed and used to isolate VP6.

Once isolated, the VP6 polypeptide can, if desired, be further purified and/or concentrated, as long as further processing does not impair antigenicity. A variety of methods for purification and concentration are well known in the art (see, e.g., Fisher, *Laboratory Techniques In Biochemistry And Molecular Biology,* eds., Work and Burdon, Elsevier 1980), including ultracentrifugation and/or precipitation (e.g., with ammonium sulfate), microfiltration (e.g., via 0.45 μm cellulose acetate filters), ultrafiltration (e.g., with the use of a sizing membrane and recirculation filtration), gel filtration (e.g., columns filled with Sepharose CL-6B, CL-4B, CL-2B, 6B, 4B or 2B, Sephacryl S-400 or S-300, Superose 6 or Ultrogel A2, A4, or A6; all available from Pharmacia), fast protein liquid chromatography (FPLC), and high performance liquid chromatography (HPLC).

II. Preparation and Administration of VP6 Polypeptides

The invention includes the use of vaccine compositions (e.g., oral vaccines) containing at least one VP6 polypeptide, and, optionally, a pharmaceutically acceptable carrier, such as the diluent phosphate buffered saline or a bicarbonate solution (e.g., 0.24 M $NaHCO_3$). The carriers used in the composition are selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, or immune-stimulating complex (ISCOM), can also be included in the new vaccine composition.

The amount of vaccine administered will depend, for example, on the particular VP6 and its antigenicity, whether an adjuvant is co-administered with the VP6, the type of adjuvant co-administered, the mode and frequency of administration, and the desired effect (e.g., protection or treatment), as can be determined by one skilled in the art. In general, the new vaccine antigens are administered in amounts ranging between 1 μg and 100 mg per adult human dose. If adjuvants are administered with the vaccines, amounts ranging between 1 ng and 1 mg per adult human dose can generally be used. Administration is repeated as necessary, as can be determined by one skilled in the art. For example, a priming dose can be followed by three booster doses at weekly intervals. A booster shot can be given at 8 to 12 weeks after the first immunization, and a second booster can be given at 16 to 20 weeks, using the same formulation. Sera or T-cells can be taken from the individual for testing the immune response elicited by the vaccine against a rotavirus. Methods of assaying antibodies or cytotoxic T-cells against a specific antigen are well known in the art. Additional boosters can be given as needed. By varying the amount of VP6 or pharmaceutical composition, the immunization protocol can be optimized for eliciting a maximal immune response.

Alternatively, the VP6 vaccine compositions can be administered as ISCOMs. Protective immunity has been generated in a variety of experimental models of infection, including toxoplasmosis and Epstein-Barr virus-induced tumors, using ISCOMS as the delivery vehicle for antigens (Mowat et al., Immunology Today 12:383 [1991]). Doses of antigen as low as 1 μg encapsulated in ISCOMs have been found to produce class I mediated cytotoxic T cell responses (Takahashi et al., Nature 344:873 [1990]). Polypeptides are delivered into cells using ISCOMS in a manner and dosage similar to that described above for liposomes.

The VP6 vaccines can be administered via any appropriate route, e.g, intravenously, intraarterially, topically by injection, intraperitoneally, intrapleurally, orally, subcutaneously, intramuscularly, sublingually, intraepidermally, or rectally.

III. Preparation and Administration of DNA Encoding VP6 Polypeptides

Instead of administering the VP6 polypeptide directly, an expression vector, such as a DNA vector, encoding the VP6 can be used as the vaccine.

A DNA vector includes at least two components: (1) VP6 coding sequence, and (2) a transcriptional promoter operatively linked for expression of the VP6. VP6-encoding DNA can encode more than one antigen, such as another VP6 from a different rotavirus. A variety of cloned VP6 sequences are readily available, including human VP6 (GenBank Accession No. U04741) and bovine VP6 (Tarlow et al., Nucl Acids Res 18:4921 [1990]).

The DNA vector can optionally include additional sequences such as enhancer elements, splicing signals, termination and polyadenylation signals, viral replicons, and bacterial plasmid sequences. Such vectors can be produced by a number of known methods. For example, DNA encoding the desired VP6 can be inserted into any number of commercially available expression vectors (see, e.g., Invitrogen Catalog, 1998).

The DNA vector can be administered to an individual, or inoculated, in the presence of adjuvants or other substances that have the capability of promoting DNA uptake or recruiting immune system cells to the site of the inoculation. For example, DNA encapsulated in microparticles have been shown to promote expression of rotaviral proteins from DNA vectors in vivo (U.S. Pat. No. 5,620,896).

An animal can be inoculated with DNA through any parenteral route, e.g., via intravenous, intraperitoneal, intradermal, subcutaneous, inhalation, or intramuscular routes, oral, or by particle bombardment using a gene gun. Muscle is a useful site for the delivery and expression of VP6-encoding DNA because animals have a proportionately large muscle mass which is conveniently accessed by direct injection through the skin. A comparatively large dose of DNA can be deposited into muscle by multiple and/or repetitive injections, for example, to extend therapy over long periods of time.

In addition, an individual can be inoculated by a mucosal route. The VP6-encoding DNA can be administered to a mucosal surface by a variety of methods including DNA-containing nose-drops, inhalants, suppositories, or microspheres. An example of oral administration of microsphere-encapsulated DNA is shown below.

A. DNA Delivery by Encapsulation in PLG Microparticles and Oral Administration

A DNA vector containing the VP6 gene can be encapsulated in poly(lactide-co-glycolide) (PLG) microparticles by a solvent extraction technique, such as the ones described in Jones et al., Infect Immun 64:489 (1996) and Jones et al., Vaccine 15:814 (1997). For example, the DNA is emulsified with PLG dissolved in dichloromethane, and this water-in-oil emulsion is emulsified with aqueous polyvinyl alcohol (an emulsion stabilizer) to form a (water-in-oil)-in-water double emulsion. This double emulsion is added to a large quantity of water to dissipate the dichloromethane, which results in the microdroplets hardening to form microparticles. These microdroplets or microparticles are harvested by centrifugation, washed several times to remove the polyvinyl alcohol and residual solvent, and finally lyophilized. The microparticles containing DNA have a mean diameter of 0.5 μm. To test for DNA content, the microparticles are dissolved in 0.1 M NaOH at 100° C. for 10 minutes. The $A_{260}$ is measured and DNA calculated from a standard curve. Incorporation of DNA into microparticles is in the range of 1.76 g to 2.7 g DNA per mg PLG.

Microparticles containing about 1 to 100 μg of DNA are suspended in about 0.1 to 1 ml of 0.1 M sodium bicarbonate, pH 8.5, and orally administered to mice by gavage.

B. DNA Delivery by Particle Bombardment

Alternatively, intradermal administration of DNA by particle bombardment can be used to deliver DNA for expression of rotavirus VP6 in skin cells. The Acyl particle bombardment device ("gene gun"; Agracetus, Middleton, Wis.) can be employed to deliver DNA-coated gold beads to the epidermis of mice.

Plasmid DNA is affixed to gold particles by adding 10 mg of 0.95 μm gold powder (Degussa, South Plainfield, N.J.), and an appropriate amount of plasmid DNA, to a 1.5 ml centrifuge tube containing 50 μl of 0.1 M spermidine. Plasmid DNA and gold is co-precipitated by the addition of 50 μl of 2.5 M $CaCl_2$ during vortex mixing, after which the precipitate is allowed to settle and washed with absolute ethanol and resuspended in 2 ml of ethanol. The gold/DNA suspension is transferred to a capped vial and immersed in a sonicating water bath for 2 to 5 seconds to resolve clumps. 163 μl of the gold/DNA suspension is layered onto 1.8 cm×1.8 cm Mylar sheets and allowed to settle for several minutes after which the meniscus is broken and excess ethanol is removed by aspiration. Gold/DNA-coated mylar sheets are dried and stored under vacuum. The total amount of DNA per sheet is a function of the DNA/gold ratio and rang from 0.2 to 0.0002 μg per sheet.

Animals are anesthetized with 30 μl of Ketaset/Rompun (10:2). Abdominal target areas are shaved and treated with NAIR® (Alkaline hair remover Carter-Wallace, N.Y.) for two minutes to remove residual stubble and stratum corneum. Target areas are thoroughly rinsed with water prior to gene delivery. DNA-coated gold particles are delivered into abdominal skin with the Acyl instrument, which employs an electric spark discharge as the motive force. Each animal receives two nonoverlapping deliveries per immunization, at a discharge voltage of 17 kV. Particle bombardment technology is presented in the following articles: Yang et al., Proc Natl Acad Sci USA 87:9568 [1990]; Yang, CRC Crit Rev Biotechnol 12:335 [1992]; and Cheng et al., Proc Natl Acad Sci USA 90:4455 [1993].

The beads deliver DNA into cells, where the DNA can be expressed (Yang et al., Proc Natl Acad Sci USA 88:2726 [1991]). Expression is transient, with most of the expression being lost within 2–3 days due to the normal sloughing of the epidermis (Williams et al., Proc Natl Acad Sci USA 88:2726 [1991]).

IV. Evaluating Vaccine Efficacy

Before administering the above vaccines in humans, toxicity and efficacy testing in animals are desirable. In an example of efficacy testing, mice (as described below) can be orally vaccinated. After the initial vaccination or after optional booster vaccinations, the mice (and corresponding control mice receiving mock vaccinations) are challenged with 100 $ID_{50}$ murine rotavirus. Efficacy is determined if mice receiving the VP6 vaccine significantly lowers the virus shed in stool. Rotavirus titers in stool can be measured using the ELISA method described in Herrmann et al., J Infect Dis 152:831 (1985). As an example, the adult mouse model as described in Ward et al., J Virol 64:5070 (1990) can be used for testing protection against rotavirus infection.

The adult mouse model is convenient in assessing protection against an infectious agent by increasing the time period within which to perform the study. In this model, adult BALB/c mice (6 weeks or older) inoculated with a rotavirus do not show disease symptoms but, instead, exhibit infection as viral shedding in the feces for approximately one week post-infection. Virus shedding in feces is conveniently measured and quantitated by an enzme-linked immunosorbent assay (ELISA). Studies involving quantitation of viral shedding in adult mice is preferred over studies in which disease symptoms are observed in infant mice because the latter studies are hindered by the short period in which infant mice are susceptible to rotavirus illness (from birth to 15 days of age).

The invention will be further described in the following example, which does not limit the scope of the invention as described in the claims.

EXAMPLE

The bovine rotavirus VP6 gene (Indiana strain) and the EDIM murine rotavirus VP6 gene were separately cloned into expression vector JW4303, which is described in Yasutomi et al., J Virol 70:678 (1996). The Indiana bovine rotavirus is described in Fernandez et al., Vaccine 14:1303 (1996) and Fernandez et al., Vaccine 16:507 (1998). The EDIM murine rotavirus VP6 sequence is available as GenBank Accession No. U36474 and has the following sequence:

(SEQ ID NO:11)

```
MDVLYSISRTLKDARDKIVEGTLYSNVSDLIQQFNQMLVTMNGNE
FQTGGIGNLPLRNWNFDFGLLGTTLLNLDANYVESARTTIDYFVD
FIDNVCMDEMVRESQRNGIAPQSDALRNVSGVKFRRINFNNSSEY
IENWNLQNRRQRTGFTFHKPNIFPYSASFTLNRSQPQHDNLMGTM
WLNAGSEIQVAGFDYSCAINAPANIQQFEHIVQLRRVLTTATITL
LPDAERFSFPRAINSADGATTWYFNPVILRPNNVEVEFLLNGQVI
NTYQARFGTIVARNFDTIRLSFQLMRPPNMTPAVTALFPNAQPFE
HHATVGLTLRIDSAICESVLADASETMLANVTSVRQEYAIPVGPV
FPPGMNWTDLITNYSPSREDNLQRVFTDASIRSMLVK
```

The JW4303 vector contains sequences from the cytomegalovirus immediate early promoter to drive transcription and sequences from bovine growth hormone genes to provide a polyadenylation signal.

To prepare the vector for cloning, the TPA leader sequence was removed by treatment with restriction endonucleases Hind III and Bam HI. The Hind III site was changed to a Bam HI site and the gene for VP6 was inserted as a Bam HI-Bam HI fragment.

The VP6 genes had been inserted in the Bam HI site of plasmid Bluescript KS- and was released by Bam HI digestion prior to insertion into plasmid JW4303. Newly constructed plasmids in the correct orientation were identified by restriction endonuclease digestion. Expression of rotavirus VP6 in transfected COS cells was confirmed by indirect immunofluorescent staining with monoclonal antibody to VP6. The monoclonal antibody had been prepared against a rotavirus SA-11 strain (Cukor et al., J Clin Microbiol 19:888 (1984). The control DNA vaccine was the plasmid without the viral cDNA insert.

To encapsulate the DNA in PLG microparticles, the DNA was emulsified with PLG dissolved in dichloromethane, and this water-in-oil emulsion was emulsified with aqueous polyvinyl alcohol (an emulsion stabilizer) to form a (water-in-oil)-in-water double emulsion. This double emulsion was added to a large quantity of water to dissipate the dichloromethane, which resulted in the microdroplets hardening to form microparticles. These were harvested by centrifugation, washed several times to remove the polyvinyl alcohol and residual solvent, and finally lyophilized. The microparticles containing DNA had a mean diameter of 0.5 $\mu$m. To test for DNA content, the microparticles were dissolved in 0.1 M NaOH at 100° C. for 10 minutes. The $A_{260}$ was measured and DNA calculated from a standard curve. Incorporation of DNA into microparticles was 1.76 g to 2.7 g DNA per mg PLG for the VP6 DNA vaccines and 1.75 g to 3.61 g per mg PLG for the plasmid control.

Microparticles containing about 50 $\mu$g of DNA were suspended in about 0.5 ml of 0.1 M sodium bicarbonate, pH 8.5, and orally administered to each BALB/c mouse by gavage. Five mice received the bovine VP6 vaccine and three mice received the murine VP6 vaccine. Four mice received the control vaccine (vector without VP6 insert, as described above).

For evaluating serum antibody responses, an indirect ELISA for total antibody (IgG, IgM, and IgA) against EDIM rotavirus was used. Intestinal IgA antibodies to EDIM virus were determined by use of IgA-specific peroxidase-labeled anti-Ig in an indirect ELISA. Both ELISA assays are described in Herrmann et al., Vaccine 15:899 (1997). Five percent (wt/vol) stool suspensions in 0.01 M phosphate buffered saline (pH 7.1) were further diluted 1:4 (final dilution of 1:80) and used for assays of fecal IgA. The level of serum antibodies against murine rotavirus was measured at various times post-immunization, and the results are shown below.

loq(1/ELISA titer)

| Weeks post- | Mice Receiving: | | |
|---|---|---|---|
| immunization | Bovine VP6 | Murine VP6 | Control |
| 0 | <2 | <2 | <2 |
| 6 | 2.30 ± 0.00 | 2.00 ± 0.00 | <2 |
| 8 | 2.15 ± 0.21 | 2.60 ± 0.42 | <2 |
| 10 | 2.60 ± 0.00 | 2.50 ± 0.46 | <2 |
| 12 | 2.30 ± 0.42 | 2.78 ± 0.16 | <2 |

The numerical values are average values for each set of mice with the 95% confidence interval as indicated.

The results indicate that the bovine VP6 DNA vaccine, as well as the murine VP6 vaccine, were capable of eliciting antibodies to murine rotavirus.

The mice described immediately above were then challenged at 12 weeks post-immunization with 100 $ID_{50}$ of EDIM murine rotavirus as described in Ward et al., J Virol 64:5070 (1990). The challenge virus was derived from epizootic diarrhea of infant mice. To monitoring viral antigen shedding in vaccinated mice feces, a monoclonal antibody-based ELISA was used as described in Herrmann et al., J Infect Dis 152:831 (1985). The viral titers are reported as $A_{450nm}$ values.

FIG. 1 shows the fecal viral loads after challenge as described above. (○) represents viral loads in mice inoculated with murine PLG-VP6 DNA; (▽) represents viral loads in mice inoculated with bovine PLG-VP6 DNA; and (●) represents viral loads in mice inoculated with PLG control DNA. A positive ELISA titer is indicated if the $A_{450nm}$ value is at least 0.1. At three and four days post-challenge, viral titers for both the bovine and murine VP6 immunized mice were significantly lower as compared to the control immunized mice. Error bars represent one standard deviation from the mean.

Statistical analyses for all values shown above were performed using a non-parametric Wilcoxon 2-sample test for ranked data, analysis of variance, and the Student-Newman-Keuls test for multiple comparison of the differences among experimental groups.

What is claimed is:

1. A method of producing a protective immune response in a bird or mammal against a first rotavirus, the method comprising:

identifying a bird or mammal susceptible to or having a first rotavirus infection;

administering to the bird or mammal an isolated VP6 polypeptide of a second rotavirus sufficient to produce a protective immune response against the first rotavirus, the second rotavirus capable of infecting a different species than the first rotavirus.

2. The method of claim 1, wherein the isolated VP6 polypeptide of the second rotavirus is administered to the bird or mammal via an expression vector comprising a nucleotide sequence encoding the VP6 polypeptide of the second rotavirus.

3. The method of claim 2, wherein the expression vector is a DNA plasmid.

4. The method of claim 2, wherein the expression vector is encapsulated in a microparticle.

5. The method of claim 4, wherein the microparticle comprises poly(lactide-co-glycolide).

6. The method of claim 2, wherein the expression vector further comprises a cytomegalovirus intron A transcriptional regulatory sequence and a cytomegalovirus enhacer and promoter sequence operably linked to the sequence encoding the VP6 polypeptide of the second rotavirus.

7. The method of claim 2, wherein the expression vector is administered orally.

8. The method of claim 1, wherein the bird or mammal is a mammal selected from the group consisting of cows, pigs, and horses.

9. The method of claim 1, wherein the bird or mammal is a human.

10. The method of claim 9, wherein the first rotavirus is capable of infecting humans.

11. The method of claim 10, wherein the second rotavirus is capable of infecting cows.

12. The method of claim 1, wherein the VP6 polypeptide cross-reacts with antibodies produced from the bird or mammal when infected with the first rotavirus.

13. A method of producing a protective immune response in a individual against a human rotavirus, the method comprising:

identifying an individual susceptible to or having a human rotavirus infection;

administering to the individual a DNA plasmid expression vector comprising a sequence encoding a VP6 polypeptide of a non-human rotavirus, the VP6 polypeptide expressed from the DNA plasmid in vivo being sufficient to produce a protective immune response in the individual against the human rotavirus.

14. The method of claim 13, wherein the DNA plasmid expression vector is administered as a microparticle.

15. The method of claim 14, wherein the microparticle comprises poly(lactide-co-glycolide).

16. The method of claim 13, wherein the non-human rotavirus is capable of infecting a mammal selected from the group consisting of a pig, cow, or horse.

17. The method of claim 16, wherein the mammal is a cow.

18. The method of claim 13, wherein the VP6 polypeptide cross-reacts with antibodies produced from the individual when infected with the human rotavirus.

19. A method of producing a protective immune response in a bird or mammal of a first species against a first rotavirus, the method comprising:

identifying a bird or mammal of a first species susceptible to or having a first rotavirus infection;

administering to the bird or mammal an isolated VP6 polypeptide of a second rotavirus sufficient to produce a protective immune response against the first rotavirus, the second rotavirus capable of infecting a second species different from the first species and incapable of infecting the first species.

20. The method of claim 19, wherein the isolated VP6 polypeptide of the second rotavirus is administered to the bird or mammal via an expression vector comprising a nucleotide sequence encoding the VP6 polypeptide of the second rotavirus.

21. The method of claim 20, wherein the expression vector is a DNA plasmid.

22. The method of claim 21, wherein the expression vector is encapsulated in a microparticle.

23. The method of claim 22, wherein the microparticle comprises poly(lactide-co-glycolide).

24. The method of claim 20, wherein the expression vector further comprises a cytomegalovirus intron A transcriptional regulatory sequence and a cytomegalovirus enhacer and promoter sequence operably linked to the sequence encoding the VP6 polypeptide of the second rotavirus.

25. The method of claim 20, wherein the expression vector is administered orally.

26. The method of claim 19, wherein the bird or mammal is a mammal selected from the group consisting of cows, pigs, and horses.

27. The method of claim 26, wherein the bird or mammal is a human.

* * * * *

SEQUENCE LISTING

```
<160> NUMBER OF SEQ ID NOS: 11

<210> SEQ ID NO 1
<211> LENGTH: 397
<212> TYPE: PRT
<213> ORGANISM: Bovine rotavirus

<400> SEQUENCE: 1

Met Asp Val Leu Tyr Ser Leu Ser Lys Thr Leu Lys Asp Ala Arg Asp
 1               5                   10                  15

Lys Ile Val Glu Gly Thr Leu Tyr Ser Asn Val Ser Asp Leu Ile Gln
             20                  25                  30

Gln Phe Asn Gln Met Ile Ile Thr Met Asn Gly Asn Glu Phe Gln Thr
         35                  40                  45

Gly Gly Ile Gly Asn Leu Pro Ile Arg Asn Trp Asn Phe Asp Phe Gly
     50                  55                  60

Leu Leu Gly Thr Thr Leu Leu Asn Leu Asp Ala Asn Tyr Val Glu Thr
 65                  70                  75                  80

Ala Arg Asn Thr Ile Asp Tyr Phe Val Asp Phe Val Asp Asn Val Cys
                 85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285
```

-continued

```
Arg Leu Ser Phe Gln Leu Met Arg Pro Pro Asn Met Thr Pro Ala Val
    290                 295                 300

Ala Ala Leu Phe Pro Asn Ala Gln Pro Phe Glu His Gln Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Val Lys
385                 390                 395


<210> SEQ ID NO 2
<211> LENGTH: 395
<212> TYPE: PRT
<213> ORGANISM: Bovine rotavirus

<400> SEQUENCE: 2


Met Asp Val Leu Phe Ser Ile Ala Lys Thr Val Ser Glu Leu Lys Lys
  1               5                  10                  15

Arg Val Val Val Gly Thr Ile Tyr Thr Asn Val Glu Asp Ile Ile Gln
            20                  25                  30

Gln Thr Asn Glu Leu Ile Arg Thr Leu Asn Gly Ser Thr Phe His Thr
        35                  40                  45

Gly Gly Ile Gly Thr Gln Pro Gln Lys Asp Trp Val Val Gln Leu Pro
     50                  55                  60

Gln Leu Gly Thr Thr Leu Leu Asn Leu Asp Asp Asn Tyr Val Gln Ser
 65                  70                  75                  80

Ala Arg Gly Ile Ile Asp Tyr Leu Ala Ser Phe Ile Glu Ala Val Cys
                 85                  90                  95

Asp Asp Glu Met Val Arg Glu Ala Ser Arg Asn Gly Met Gln Pro Gln
            100                 105                 110

Ser Pro Thr Leu Ile Ala Leu Ala Ser Ser Lys Phe Lys Thr Ile Asn
        115                 120                 125

Phe Asn Asn Ser Ser Gln Ser Ile Lys Asn Trp Ser Ala Gln Ser Arg
    130                 135                 140

Arg Glu Asn Pro Val Tyr Glu Tyr Lys Asn Pro Met Val Phe Glu Tyr
145                 150                 155                 160

Arg Asn Ser Tyr Ile Leu His Arg Ala Asp Gln Gln Phe Gly Asn Ala
                165                 170                 175

Met Gly Leu Arg Tyr Tyr Thr Thr Ser Asn Thr Cys Gln Ile Ala Ala
            180                 185                 190

Phe Asp Ser Thr Met Ala Glu Asn Ala Pro Asn Asn Thr Gln Arg Phe
        195                 200                 205

Ile Tyr His Gly Arg Leu Lys Arg Pro Ile Ser Asn Val Leu Met Lys
    210                 215                 220

Val Glu Arg Gly Ala Pro Asn Val Asn Asn Pro Thr Ile Leu Pro Asp
225                 230                 235                 240

Pro Thr Asn Gln Thr Thr Trp Leu Phe Asn Pro Val Gln Val Met Asn
                245                 250                 255
```

-continued

```
Gly Thr Phe Thr Ile Glu Phe Tyr Asn Asn Gly Gln Leu Val Asp Met
            260                 265                 270

Val Arg Asn Met Gly Ile Ala Thr Val Arg Thr Phe Asp Ser Tyr Arg
        275                 280                 285

Ile Thr Ile Asp Met Ile Arg Pro Ala Ala Met Thr Gln Tyr Val Gln
    290                 295                 300

Gln Leu Phe Pro Val Gly Gly Pro Tyr Ser His Gln Ala Ala Tyr Met
305                 310                 315                 320

Leu Thr Leu Ser Val Leu Asp Ala Thr Thr Glu Ser Val Leu Cys Asp
                325                 330                 335

Ser His Ser Val Asp Tyr Ser Ile Val Ala Asn Thr Arg Arg Asp Ser
            340                 345                 350

Ala Met Pro Ala Gly Thr Val Phe Gln Pro Gly Phe Pro Trp Glu Gln
        355                 360                 365

Thr Leu Ser Asn Tyr Thr Val Ala Gln Glu Asp Asn Leu Glu Arg Leu
    370                 375                 380

Leu Leu Val Ala Ser Val Lys Arg Met Val Met
385                 390                 395


<210> SEQ ID NO 3
<211> LENGTH: 397
<212> TYPE: PRT
<213> ORGANISM: Human rotavirus

<400> SEQUENCE: 3


Met Glu Val Leu Tyr Ser Leu Ser Lys Thr Leu Lys Asp Ala Arg Asp
  1               5                  10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Val Arg Asn Trp Thr Phe Asp Phe Gly
    50                  55                  60

Leu Leu Gly Thr Thr Leu Leu Asn Leu Asp Ala Asn Tyr Val Glu Asn
 65                  70                  75                  80

Ala Arg Thr Ile Ile Glu Tyr Phe Ile Asp Phe Ile Asp Asn Val Cys
                85                  90                  95

Met Asp Glu Met Ala Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220
```

-continued

```
Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Ala Ile
        275                 280                 285

Arg Leu Leu Phe Gln Leu Met Arg Pro Pro Asn Met Thr Pro Ala Val
    290                 295                 300

Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395


<210> SEQ ID NO 4
<211> LENGTH: 395
<212> TYPE: PRT
<213> ORGANISM: Human rotavirus

<400> SEQUENCE: 4


Met Asp Val Leu Phe Ser Ile Ala Lys Thr Val Ser Asp Leu Lys Lys
  1               5                  10                  15

Lys Val Val Val Gly Thr Ile Tyr Thr Asn Val Glu Asp Val Val Gln
             20                  25                  30

Gln Thr Asn Glu Leu Ile Arg Thr Leu Asn Gly Asn Ile Phe His Thr
         35                  40                  45

Gly Gly Ile Gly Thr Gln Pro Gln Lys Glu Trp Asn Phe Gln Leu Pro
     50                  55                  60

Gln Leu Gly Thr Thr Leu Leu Asn Leu Asp Asp Asn Tyr Val Gln Ser
 65                  70                  75                  80

Thr Arg Gly Ile Ile Asp Phe Leu Ser Ser Phe Ile Glu Ala Val Cys
                 85                  90                  95

Asp Asp Glu Ile Val Arg Glu Ala Ser Arg Asn Gly Met Gln Pro Gln
            100                 105                 110

Ser Pro Ala Leu Ile Leu Leu Ser Ser Ser Lys Phe Lys Thr Ile Asn
        115                 120                 125

Phe Asn Asn Ser Ser Gln Ser Ile Lys Asn Trp Asn Ala Gln Ser Arg
    130                 135                 140

Arg Glu Asn Pro Val Tyr Glu Tyr Lys Asn Pro Met Leu Phe Glu Tyr
145                 150                 155                 160

Lys Asn Ser Tyr Ile Leu Gln Arg Ala Asn Pro Gln Phe Gly Ser Val
                165                 170                 175

Met Gly Leu Arg Tyr Tyr Thr Thr Ser Asn Thr Cys Gln Ile Ala Ala
            180                 185                 190
```

-continued

Phe Asp Ser Thr Leu Ala Glu Asn Ala Pro Asn Asn Thr Gln Arg Phe
195 200 205

Val Tyr Asn Gly Arg Leu Lys Arg Pro Ile Ser Asn Val Leu Met Lys
210 215 220

Ile Glu Ala Gly Ala Pro Asn Ile Ser Asn Pro Thr Ile Leu Pro Asp
225 230 235 240

Pro Asn Asn Gln Thr Thr Trp Leu Phe Asn Pro Val Gln Leu Met Asn
245 250 255

Gly Thr Phe Thr Ile Glu Phe Tyr Asn Asn Gly Gln Leu Ile Asp Met
260 265 270

Val Arg Asn Met Gly Ile Val Thr Val Arg Thr Phe Asp Ser Tyr Arg
275 280 285

Ile Thr Ile Asp Met Ile Arg Pro Ala Ala Met Thr Gln Tyr Val Gln
290 295 300

Arg Ile Phe Pro Gln Gly Gly Pro Tyr His Phe Gln Ala Thr Tyr Met
305 310 315 320

Leu Thr Leu Ser Ile Leu Asp Ala Thr Thr Glu Ser Val Leu Cys Asp
325 330 335

Ser His Ser Val Glu Tyr Ser Ile Val Ala Asn Val Arg Arg Asp Ser
340 345 350

Ala Met Pro Ala Gly Thr Val Phe Gln Pro Gly Phe Pro Trp Glu His
355 360 365

Thr Leu Ser Asn Tyr Thr Val Ala Gln Glu Asp Asn Leu Glu Arg Leu
370 375 380

Leu Leu Ile Ala Ser Val Lys Arg Met Val Met
385 390 395

<210> SEQ ID NO 5
<211> LENGTH: 397
<212> TYPE: PRT
<213> ORGANISM: Porcine rotavirus

<400> SEQUENCE: 5

Met Glu Val Leu Tyr Ser Leu Ser Lys Thr Leu Lys Asp Ala Arg Asp
1 5 10 15

Lys Ile Val Glu Gly Thr Leu Tyr Ser Asn Val Ser Asp Leu Ile Gln
20 25 30

Gln Phe Asn Gln Met Ile Val Thr Met Asn Gly Asn Asp Phe Gln Thr
35 40 45

Gly Gly Ile Gly Asn Ser Pro Val Arg Asn Trp Asn Phe Asp Phe Gly
50 55 60

Leu Leu Gly Thr Thr Leu Leu Asn Leu Asp Ala Asn Tyr Val Glu Asn
65 70 75 80

Ala Arg Thr Thr Ile Glu Tyr Phe Val Asp Phe Ile Asp Asn Val Cys
85 90 95

Met Asp Glu Met Thr Arg Glu Ser Gln Arg Ser Gly Ile Ala Pro Gln
100 105 110

Ser Glu Ala Leu Arg Lys Gln Ser Gly Ile Lys Phe Lys Arg Ile Asn
115 120 125

Phe Asp Asn Ser Ser Asp Tyr Ile Glu Asn Trp Asn Leu Gln Asn Arg
130 135 140

Arg Gln Arg Thr Gly Phe Val Phe His Lys Pro Asn Ile Leu Pro Tyr
145 150 155 160

-continued

```
Ser Ala Ser Phe Thr Leu Asn Arg Ser Gln Pro Ala His Asp Asn Leu
                165                 170                 175

Met Gly Thr Met Trp Ile Asn Ala Gly Ser Glu Ile Gln Val Ala Gly
            180                 185                 190

Phe Asp Tyr Ser Cys Ala Phe Asn Ala Pro Ala Asn Ile Gln Gln Phe
        195                 200                 205

Glu His Val Val Pro Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Thr Thr Thr Trp Tyr Phe Asn Pro Val Ile Leu Arg Pro
                245                 250                 255

Ser Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285

Arg Leu Ser Phe Gln Leu Val Arg Pro Pro Asn Met Thr Pro Ala Val
    290                 295                 300

Ala Asn Leu Phe Pro Gln Ala Pro Pro Phe Ile Phe His Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Leu Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395


<210> SEQ ID NO 6
<211> LENGTH: 397
<212> TYPE: PRT
<213> ORGANISM: Murine rotavirus

<400> SEQUENCE: 6


Met Asp Val Leu Tyr Ser Ile Ser Arg Thr Leu Lys Asp Ala Arg Asp
  1               5                  10                  15

Lys Ile Val Glu Gly Thr Leu Tyr Ser Asn Val Ser Asp Leu Ile Gln
             20                  25                  30

Gln Phe Asn Gln Met Leu Val Thr Met Asn Gly Asn Glu Phe Gln Thr
         35                  40                  45

Gly Gly Ile Gly Asn Leu Pro Leu Arg Asn Trp Asn Phe Asp Phe Gly
     50                  55                  60

Leu Leu Gly Thr Thr Leu Leu Asn Leu Asp Ala Asn Tyr Val Glu Ser
 65                  70                  75                  80

Ala Arg Thr Thr Ile Asp Tyr Phe Val Asp Phe Ile Asp Asn Val Cys
                 85                  90                  95

Met Asp Glu Met Met Arg Glu Ser Gln Arg Asn Gly Ile Ala Pro Gln
            100                 105                 110

Ser Asp Ala Leu Arg Lys Leu Ser Gly Val Lys Phe Arg Arg Ile Asn
        115                 120                 125
```

-continued

```
Phe Asn Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Gln His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Val Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300

Thr Ala Leu Phe Pro Asn Ala Gln Pro Phe Glu His His Ala Thr Val
305                 310                 315                 320

Gly Leu Thr Leu Arg Ile Asp Ser Ala Ile Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Val Lys
385                 390                 395


<210> SEQ ID NO 7
<211> LENGTH: 397
<212> TYPE: PRT
<213> ORGANISM: Avian rotavirus

<400> SEQUENCE: 7

Met Asp Val Leu Tyr Ser Leu Ala Lys Thr Leu Lys Asp Ala Arg Ala
  1               5                  10                  15

Lys Ile Val Glu Gly Thr Leu Tyr Thr Asn Val Ala Asp Ile Val Gln
             20                  25                  30

Gln Val Asn Gln Val Ile Asn Ser Ile Asn Gly Ser Thr Phe Gln Thr
         35                  40                  45

Gly Gly Ile Gly Asn Leu Pro Val Arg Asn Trp Thr Phe Asp Phe Gly
     50                  55                  60

Thr Leu Gly Thr Thr Leu Leu Asn Leu Asp Ala Asn Tyr Val Glu Asn
 65                  70                  75                  80

Ala Arg Thr Thr Ile Asp Tyr Phe Ile Asp Phe Val Asp Ser Val Cys
                 85                  90                  95
```

-continued

```
Val Asp Glu Ile Val Arg Glu Ser Gln Arg Asn Gly Ile Ala Pro Gln
            100                 105                 110

Ser Asp Ser Leu Arg Gln Leu Ser Asn Ala Lys Tyr Lys Arg Ile Asn
        115                 120                 125

Tyr Asp Asn Glu Ser Glu Tyr Ile Glu Asn Trp Asn Leu Gln Asn Arg
    130                 135                 140

Arg Gln Arg Thr Gly Tyr Leu Leu His Lys Pro Asn Ile Leu Pro Tyr
145                 150                 155                 160

Asn Asn Ser Phe Thr Leu Thr Arg Ser Gln Pro Ala His Asp Asn Val
                165                 170                 175

Cys Gly Thr Ile Trp Leu Asn Asn Gly Ser Glu Ile Glu Ile Ala Gly
            180                 185                 190

Phe Asp Ser Glu Cys Ala Leu Asn Ala Pro Gly Asn Ile Gln Glu Phe
        195                 200                 205

Glu His Val Val Pro Met Arg Arg Val Leu Asn Asn Ala Thr Val Ser
    210                 215                 220

Leu Leu Pro Tyr Ala Pro Arg Leu Thr Gln Arg Ala Val Ile Pro Thr
225                 230                 235                 240

Ala Asp Gly Leu Asn Thr Trp Leu Phe Asn Pro Ile Ile Leu Arg Pro
                245                 250                 255

Asn Asn Val Gln Val Glu Phe Leu Leu Asn Gly Gln Val Ile Thr Asn
            260                 265                 270

Tyr Gln Ala Arg Tyr Gly Thr Leu Ala Ala Arg Asn Phe Asp Ser Ile
        275                 280                 285

Arg Ile Ser Phe Gln Leu Val Arg Pro Pro Asn Met Thr Pro Gly Val
    290                 295                 300

Ala Ala Leu Phe Pro Gln Ala Ala Pro Phe Pro Asn His Ala Thr Val
305                 310                 315                 320

Gly Leu Thr Leu Lys Ile Glu Ser Ala Ser Cys Glu Ser Val Leu Ser
                325                 330                 335

Asp Ala Asn Glu Pro Tyr Leu Ser Ile Val Thr Gly Leu Arg Gln Glu
            340                 345                 350

Tyr Ala Ile Pro Val Gly Pro Val Phe Pro Ala Gly Met Asn Trp Thr
        355                 360                 365

Glu Leu Leu Asn Asn Tyr Ser Ala Ser Arg Glu Asp Asn Leu Gln Arg
    370                 375                 380

Ile Phe Thr Ala Ala Ser Ile Arg Ser Met Val Ile Lys
385                 390                 395


<210> SEQ ID NO 8
<211> LENGTH: 397
<212> TYPE: PRT
<213> ORGANISM: Equine rotavirus

<400> SEQUENCE: 8


Met Glu Val Leu Tyr Ser Ile Ser Lys Thr Leu Lys Asp Ala Arg Asp
  1               5                  10                  15

Lys Ile Val Glu Gly Thr Leu Tyr Ser Asn Val Ser Asp Ile Ile Gln
             20                  25                  30

Gln Phe Asn Gln Ile Ile Val Thr Met Asn Gly Asn Glu Phe Gln Thr
         35                  40                  45

Gly Gly Ile Gly Thr Leu Pro Ile Arg Asn Trp Thr Phe Asp Phe Gly
     50                  55                  60
```

-continued

Leu Leu Gly Thr Thr Leu Leu Asn Leu Asp Ala Asn Tyr Val Glu Thr
65 70 75 80

Ala Arg Thr Thr Ile Glu Tyr Phe Ile Asp Phe Ile Asp Asn Val Cys
85 90 95

Met Asp Glu Met Thr Arg Glu Ser Gln Arg Asn Gly Ile Ala Pro Gln
100 105 110

Ser Asp Ala Leu Arg Lys Leu Ser Gly Ile Lys Phe Lys Arg Ile Asn
115 120 125

Phe Asp Asn Ser Ser Glu Tyr Ile Glu Asn Trp Asn Leu Gln Asn Arg
130 135 140

Arg Gln Arg Thr Gly Phe Val Phe His Lys Pro Asn Ile Phe Pro Tyr
145 150 155 160

Ser Ala Ser Phe Thr Leu Asn Arg Ser Gln Pro Leu His Asn Asp Leu
165 170 175

Met Gly Thr Met Trp Leu Asn Ala Gly Ser Glu Ile Gln Val Ala Gly
180 185 190

Phe Asp Tyr Ser Cys Ala Ile Asn Ala Pro Ala Asn Thr Gln Gln Phe
195 200 205

Glu His Ile Val Gln Leu Arg Arg Ala Leu Thr Thr Ala Thr Ile Thr
210 215 220

Ile Leu Pro Asp Ala Glu Arg Phe Ser Phe Pro Arg Val Ile Asn Ser
225 230 235 240

Ala Asp Gly Ala Thr Thr Trp Phe Phe Asn Pro Val Ile Leu Arg Pro
245 250 255

Asn Asn Val Glu Val Glu Phe Leu Leu Asn Gly Gln Ile Ile Asn Thr
260 265 270

Tyr Gln Ala Arg Phe Gly Thr Ile Ile Ala Arg Asn Phe Asp Thr Ile
275 280 285

Arg Leu Ser Phe Gln Leu Met Arg Pro Pro Asn Met Thr Pro Ala Val
290 295 300

Asn Ala Leu Phe Pro Gln Ala Gln Pro Phe Gln His His Ala Thr Val
305 310 315 320

Gly Leu Thr Leu Arg Ile Asp Ser Ala Val Cys Glu Ser Val Leu Ala
325 330 335

Asp Ser Asn Glu Thr Met Leu Ala Asn Val Thr Ala Val Arg Gln Glu
340 345 350

Tyr Ala Val Pro Val Gly Pro Val Phe Pro Pro Gly Met Asn Trp Thr
355 360 365

Glu Leu Ile Thr Asn Tyr Ser Pro Ser Arg Glu Asp Asn Leu Gln Arg
370 375 380

Val Phe Thr Val Ala Ser Ile Arg Ser Met Leu Ile Lys
385 390 395

<210> SEQ ID NO 9
<211> LENGTH: 397
<212> TYPE: PRT
<213> ORGANISM: Bovidae ovis rotavirus

<400> SEQUENCE: 9

Met Asp Val Leu Tyr Ser Leu Ser Lys Thr Leu Lys Asp Ala Arg Asp
1 5 10 15

Lys Ile Val Glu Gly Thr Leu Tyr Ser Asn Val Ser Asp Leu Ile Gln
20 25 30

-continued

```
Gln Phe Asn Gln Met Ile Val Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Glu Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285

Arg Leu Ser Phe Gln Leu Met Arg Pro Pro Asn Met Thr Pro Ala Val
    290                 295                 300

Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395
```

<210> SEQ ID NO 10
<211> LENGTH: 794
<212> TYPE: PRT
<213> ORGANISM: Simian rotavirus -continued

<400> SEQUENCE: 10

```
Met Asp Val Leu Tyr Ser Leu Ser Lys Thr Leu Lys Asp Ala Arg Asp
  1               5                  10                  15

Lys Ile Val Glu Gly Thr Leu Tyr Ser Asn Val Ser Asp Leu Ile Gln
             20                  25                  30

Gln Phe Asn Gln Met Ile Ile Thr Met Asn Gly Asn Glu Phe Gln Thr
         35                  40                  45

Gly Gly Ile Gly Asn Leu Pro Ile Arg Asn Trp Asn Phe Asn Phe Gly
     50                  55                  60

Leu Leu Gly Thr Thr Leu Leu Asn Leu Asp Ala Asn Tyr Val Glu Thr
 65                  70                  75                  80

Ala Arg Asn Thr Ile Asp Tyr Phe Val Asp Phe Val Asp Asn Val Cys
                 85                  90                  95

Met Asp Glu Met Val Arg Glu Ser Gln Arg Asn Gly Ile Ala Pro Gln
            100                 105                 110

Ser Asp Ser Leu Arg Lys Leu Ser Ala Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Pro Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300

Ala Val Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
                325                 330                 335

Asp Ala Ser Glu Thr Leu Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys Met Asp Val
385                 390                 395                 400
```

-continued

```
Leu Tyr Ser Leu Ser Lys Thr Leu Lys Asp Ala Arg Asp Lys Ile Val
                405                 410                 415

Glu Gly Thr Leu Tyr Ser Asn Val Ser Asp Leu Ile Gln Gln Phe Asn
            420                 425                 430

Gln Met Ile Ile Thr Met Asn Gly Asn Glu Phe Gln Thr Gly Gly Ile
        435                 440                 445

Gly Asn Leu Pro Ile Arg Asn Trp Asn Phe Asn Phe Gly Leu Leu Gly
    450                 455                 460

Thr Thr Leu Leu Asn Leu Asp Ala Asn Tyr Val Glu Thr Ala Arg Asn
465                 470                 475                 480

Thr Ile Asp Tyr Phe Val Asp Phe Val Asp Asn Val Cys Met Asp Glu
                485                 490                 495

Met Val Arg Glu Ser Gln Arg Asn Gly Ile Ala Pro Gln Ser Asp Ser
            500                 505                 510

Leu Arg Lys Leu Ser Ala Ile Lys Phe Lys Arg Ile Asn Phe Asp Asn
        515                 520                 525

Ser Ser Glu Tyr Ile Glu Asn Trp Asn Leu Gln Asn Arg Arg Gln Arg
    530                 535                 540

Thr Gly Phe Thr Phe His Lys Pro Asn Ile Phe Pro Tyr Ser Ala Ser
545                 550                 555                 560

Phe Thr Leu Asn Arg Ser Gln Pro Ala His Asp Asn Leu Met Gly Thr
                565                 570                 575

Met Trp Leu Asn Ala Gly Ser Glu Ile Gln Val Ala Gly Phe Asp Tyr
            580                 585                 590

Ser Cys Ala Ile Asn Ala Pro Ala Asn Ile Gln Gln Phe Glu His Ile
        595                 600                 605

Val Pro Leu Arg Arg Val Leu Thr Thr Ala Thr Ile Thr Leu Leu Pro
    610                 615                 620

Asp Ala Glu Arg Phe Ser Phe Pro Arg Val Ile Asn Ser Ala Asp Gly
625                 630                 635                 640

Ala Thr Thr Trp Phe Phe Asn Pro Val Ile Leu Arg Pro Asn Asn Val
                645                 650                 655

Glu Val Glu Phe Leu Leu Asn Gly Gln Ile Ile Asn Thr Tyr Gln Ala
            660                 665                 670

Arg Phe Gly Thr Ile Val Ala Arg Asn Phe Asp Thr Ile Arg Leu Ser
        675                 680                 685

Phe Gln Leu Met Arg Pro Pro Asn Met Thr Pro Ala Val Ala Val Leu
    690                 695                 700

Phe Pro Asn Ala Gln Pro Phe Glu His His Ala Thr Val Gly Leu Thr
705                 710                 715                 720

Leu Arg Ile Glu Ser Ala Val Cys Glu Ser Val Leu Ala Asp Ala Ser
                725                 730                 735

Glu Thr Leu Leu Ala Asn Val Thr Ser Val Arg Gln Glu Tyr Ala Ile
            740                 745                 750

Pro Val Gly Pro Val Phe Pro Pro Gly Met Asn Trp Thr Asp Leu Ile
        755                 760                 765

Thr Asn Tyr Ser Pro Ser Arg Glu Asp Asn Leu Gln Arg Val Phe Thr
    770                 775                 780

Val Ala Ser Ile Arg Ser Met Leu Ile Lys
785                 790
```

-continued

<210> SEQ ID NO 11
<211> LENGTH: 397
<212> TYPE: PRT
<213> ORGANISM: Murine rotavirus

<400> SEQUENCE: 11

```
Met Asp Val Leu Tyr Ser Ile Ser Arg Thr Leu Lys Asp Ala Arg Asp
  1               5                  10                  15

Lys Ile Val Glu Gly Thr Leu Tyr Ser Asn Val Ser Asp Leu Ile Gln
             20                  25                  30

Gln Phe Asn Gln Met Leu Val Thr Met Asn Gly Asn Glu Phe Gln Thr
         35                  40                  45

Gly Gly Ile Gly Asn Leu Pro Leu Arg Asn Trp Asn Phe Asp Phe Gly
     50                  55                  60

Leu Leu Gly Thr Thr Leu Leu Asn Leu Asp Ala Asn Tyr Val Glu Ser
 65                  70                  75                  80

Ala Arg Thr Thr Ile Asp Tyr Phe Val Asp Phe Ile Asp Asn Val Cys
                 85                  90                  95

Met Asp Glu Met Val Arg Glu Ser Gln Arg Asn Gly Ile Ala Pro Gln
            100                 105                 110

Ser Asp Ala Leu Arg Asn Val Ser Gly Val Lys Phe Arg Arg Ile Asn
        115                 120                 125

Phe Asn Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Gln His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Ala Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Val Ile Asn Thr
            260                 265                 270

Tyr Gln Ala Arg Phe Gly Thr Ile Val Ala Arg Asn Phe Asp Thr Ile
        275                 280                 285

Arg Leu Ser Phe Gln Leu Met Arg Pro Pro Asn Met Thr Pro Ala Val
    290                 295                 300

Thr Ala Leu Phe Pro Asn Ala Gln Pro Phe Glu His His Ala Thr Val
305                 310                 315                 320

Gly Leu Thr Leu Arg Ile Asp Ser Ala Ile Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365
```

-continued

| | | | | | | | | | | | | | | | |
|---|---|---|---|---|---|---|---|---|---|---|---|---|---|---|---|
| Asp | Leu | Ile | Thr | Asn | Tyr | Ser | Pro | Ser | Arg | Glu | Asp | Asn | Leu | Gln | Arg |
| | 370 | | | | | 375 | | | | | 380 | | | | |
| Val | Phe | Thr | Asp | Ala | Ser | Ile | Arg | Ser | Met | Leu | Val | Lys | | | |
| 385 | | | | | 390 | | | | | 395 | | | | | |